US008343473B2

(12) United States Patent
Youngblood et al.

(10) Patent No.: US 8,343,473 B2
(45) Date of Patent: Jan. 1, 2013

(54) HYDROPHILIZED ANTIMICROBIAL POLYMERS

(75) Inventors: Jeffrey P. Youngblood, Crawfordsville, IN (US); Philippe H. Sellenet, Nancy (FR); Thomas R. Stratton, Brooklyn, OH (US)

(73) Assignee: Purdue Research Foundation, West Lafayette, IN (US)

( * ) Notice: Subject to any disclaimer, the term of this patent is extended or adjusted under 35 U.S.C. 154(b) by 455 days.

(21) Appl. No.: 12/549,004

(22) Filed: Aug. 27, 2009

(65) Prior Publication Data

US 2009/0311302 A1 Dec. 17, 2009

Related U.S. Application Data

(63) Continuation-in-part of application No. 11/509,915, filed on Aug. 24, 2006.

(60) Provisional application No. 60/711,234, filed on Aug. 24, 2005.

(51) Int. Cl.
*A61K 31/00* (2006.01)

(52) U.S. Cl. .................. 424/78.3; 424/78.32; 424/78.36

(58) Field of Classification Search ........................ None
See application file for complete search history.

(56) References Cited

U.S. PATENT DOCUMENTS

| | | | |
|---|---|---|---|
| 4,414,353 A * | 11/1983 | Maslanka et al. ............ | 524/458 |
| 4,459,289 A | 7/1984 | Maltz | |
| 4,482,680 A | 11/1984 | Sheldon et al. | |
| 4,931,522 A | 6/1990 | Catena | |
| 5,317,063 A | 5/1994 | Komatsu et al. | |
| 5,509,899 A | 4/1996 | Fan et al. | |
| 6,221,425 B1 | 4/2001 | Michal et al. | |
| 6,358,557 B1 | 3/2002 | Wang et al. | |
| 6,537,663 B1 | 3/2003 | Chang et al. | |
| 6,559,116 B1 | 5/2003 | Godfroid et al. | |
| 6,689,856 B2 | 2/2004 | L'alloret | |
| 6,815,074 B2 | 11/2004 | Aguado et al. | |
| 6,815,502 B1 | 11/2004 | Lang et al. | |
| 6,852,353 B2 | 2/2005 | Qiu et al. | |
| 7,112,559 B1 | 9/2006 | Mayhall et al. | |
| 2001/0044482 A1 | 11/2001 | Hu et al. | |
| 2002/0086160 A1 | 7/2002 | Qiu et al. | |
| 2003/0091641 A1 | 5/2003 | Tiller et al. | |
| 2003/0229185 A1 | 12/2003 | Chen et al. | |
| 2003/0236376 A1 | 12/2003 | Kindt-Larsen et al. | |
| 2004/0009136 A1* | 1/2004 | Dubief et al. ............ | 424/70.11 |
| 2004/0135967 A1 | 7/2004 | Carney et al. | |
| 2004/0202639 A1 | 10/2004 | DeGrado et al. | |
| 2005/0008676 A1 | 1/2005 | Qiu et al. | |
| 2005/0008839 A1 | 1/2005 | Cramer et al. | |
| 2005/0013842 A1 | 1/2005 | Qiu et al. | |
| 2005/0032931 A1 | 2/2005 | Naisby et al. | |
| 2005/0053569 A1 | 3/2005 | Bavouzet et al. | |
| 2005/0058844 A1 | 3/2005 | Rubner et al. | |
| 2005/0101740 A1* | 5/2005 | Mougin ........................ | 525/242 |

FOREIGN PATENT DOCUMENTS

EP 375350 A2 * 6/1990
EP 0 604 369 A1 6/1994

OTHER PUBLICATIONS

Kawabata et al., "Antibacterial Activity of Soluble Pyridinium-Type Polymers", Appl. Environ. Microbiol., vol. 54, No. 10, pp. 2532-2535, Oct. 1988.
Li et al., "Effect of the Macromolecular Chain Structure of a Soluble Pyridinium-Type Polymer on Antimicrobial Activity", pp. 175-176, National American Chemical Society Meeting, Anaheim, CA, Mar. 21-25, 1999.
Li et al., "Bactericidal Ability of a Soluble Pyridinium-Type Polymer Under Different Conditions", pp. 177-178, National American Chemical Society Meeting, Anaheim, CA, Mar. 21-25, 1999.
Tiller et al., "Designing Surfaces That Kill Bacteria on Contact", Proc. Natl. Acad. Sci. USA, vol. 98, No. 11, pp. 5981-5985, May 22, 2001.
Lin et al., "Insights Into Bactericidal Action of Surface-Attached Poly(vinyl-N-hexylpyridinium) Chains", Biotechnol. Lett., vol. 24, No. 10, pp. 801-805, May 2002.
Borman, "Surfaces Designed to Kill Bacteria", Chemical & Engineering News, vol. 80, No. 22, pp. 36-38, Jun. 10, 2002.
Tiller et al., "Polymer Surfaces Derivatized With Poly(Vinyl-N-Hexylpyridinium) Kill Airborne and Waterborne Bacteria", Biotech. Bioeng., vol. 79, No. 4, pp. 465-471, Aug. 20, 2002.
Abel et al., "Preparation and Investigation of Antibacterial Carbohydrate-Based Surfaces", Carbohydr. Res., vol. 337, No. 24, pp. 2495-2499, Nov. 29, 2002.
Lin et al., "Mechanism of Bactericidal and Fungicidal Activities of Textiles Covalently Modified With Alkylated Polyethylenimine", Biotech. Bioeng., vol. 83, No. 2, pp. 168-172, Jul. 20, 2003.
Wynne et al., "Novel Polymer Bound Bactericidal Surfaces", vol. 45, No. 2, p. 521, Fall National American Chemical Society Meeting, Philadelphia, PA, Aug. 22-27, 2004.
Krishnan et al., "Antibacterial Coatings Based on Quaternized Poly(4-Vinylpyridine) Block Copolymers", Polymeric Materials: Science and Engineering, vol. 91, pp. 814-815, 2004.
Sellenet, "Hydrophilized Bactericidal Polymers", Thesis, Purdue University, MSE, Dec. 2004.
Selected Abstracts, Dec. 2004-Mar. 2005.

(Continued)

*Primary Examiner* — James Rogers
(74) *Attorney, Agent, or Firm* — K&L Gates LLP

(57) ABSTRACT

A bactericidal or antimicrobial polymeric composition includes a hydrophilic first comonomer copolymerized to a second comonomer to produce a polymeric composition that is more hydrophilic or more bactericidal or antimicrobial in an aqueous solution than either of the comonomers alone. Methods for identifying bactericidal or antimicrobial polymers, methods for rendering materials bactericidal or antimicrobial, and methods for using bactericidal or antimicrobial compositions to kill or reduce bacterial or microbial growth are also described. Applications for the inventive compositions include their use in catheters, stents, medical devices, contact lenses; root canal fillers; fibers; paper; and/or wound dressing.

15 Claims, 5 Drawing Sheets

OTHER PUBLICATIONS

Sellenet et al., "Hydrophilized Pyridinium Bactericidal Polymers", Fall National American Chemical Society Meeting, Washington, DC, Aug. 28-Sep. 1, 2005.

Sellenet et al., "Synergistic Activity of Hydrophilic Modification in Antibiotic Polymers" Biomacromolecules 2007, 8, 19-23.

Allison et al., "Hemocompatibility of Hydrophilic Antimicrobial Copolymers of Alkylated 4-Vinylpyridine" Biomacromolecules 2007, 8, 2995-2999.

* cited by examiner

HYDROPHILIZED ANTIMICROBIAL POLYMERS

The present patent document is a continuation-in-part of application Ser. No. 11/509,915, filed Aug. 24, 2006, which claims the benefit of the filing date under 35 U.S.C. §119(e) of Provisional U.S. Patent Application Ser. No. 60/711,234, filed Aug. 24, 2005. All of the foregoing applications are hereby incorporated by reference.

BACKGROUND

There is an ever-growing demand for materials suitable for killing harmful microorganisms. Such materials could be used to coat surfaces of common objects touched by people to render them antiseptic so as to prevent transmission of bacterial infections or to facilitate the killing of microorganisms in solution.

Various polycations are known to have bactericidal properties. However, their bactericidal properties can be strongly influenced by whether the polycation or a composition containing the polycation is soluble. In some instances the bactericidal property is most apparent in an insoluble form, which is not particularly amenable to killing microorganisms. In other instances the bactericidal activity is lost when the polycation is cross-linked or otherwise rendered insoluble. Application of bactericidal polymers may also be limited by their use in brushes, their insolubility in solution, or by their unfavorable biocompatibility characteristics. Accordingly, there is a need for bactericidal formulations possessing having improved bactericidal, hydrophilicity/wettability and biocompatibility characteristics suitable for rendering materials or areas bactericidal and for killing airborne and/or waterborne microorganisms.

BRIEF SUMMARY

The present invention is directed to polymeric compositions providing improved bactericidal or antimicrobial, hydrophilicity/wettability, and biocompatibility characteristics. In particular, the present invention provides a bactericidal or antimicrobial composition, including a hydrophilic first comonomer polymerized to a second comonomer to form a polymeric composition, where the polymeric composition is more soluble and/or more bactericidal or antimicrobial in an aqueous solution than either of the first comonomer or the second comonomer alone.

In a particular example, the present invention provides a quaternized bactericidal or antimicrobial composition, in which poly(4-vinylpyridine) (PVP) is copolymerized with hydroxyethylmethacrylate (HEMA) or poly(ethyleneglycol) methacrylate (PEGMA).

In another example, the present invention provides an aqueous composition comprising a polymeric composition formed from a hydrophilic first comonomer polymerized to a second comonomer; and water. The second comonomer comprises polycationic species, polycationic derivatives or combinations therefrom. In some aspects the composition further comprises a neutral thickener or cationic thickener. In some aspects, the polymeric composition is more hydrophilic than either of the first comonomer or the second comonomer alone and/or where the polymeric composition is more bactericidal or antimicrobial than either of the first comonomer or the second comonomer alone. Preferably the hydrophilic first comonomer comprises hydroxyethylmethacrylate or poly(ethyleneglycol) methacrylate; the second comonomer plurality of quaternary ammonium groups, more preferably quaternized poly(4-vinylpyridine); and the thickener is selected from the group consisting of natural gums, pectins, alginates, gelatins, carageenans, flours, starches, dextrins, casein, cellulose derivatives, polyvinyl pyrrolidones, polyaminoalkyl methacrylates, and polyaminoalkyl acrylates, preferably a cellulose derivative, more preferably hydroxyethyl cellulose.

In another example, the present invention provides a method for rendering a material or area bactericidal or antimicrobial in which a bactericidal or antimicrobial composition of the present invention is applied to a medium or device in an amount suitable for killing or significantly reducing the number of bacteria or microorganisms in or on the treated medium or device compared to an untreated medium or device.

In another example, the present invention provides a method for killing or significantly reducing the number of bacteria or microorganisms on a material or area treated with a bactericidal or antimicrobial composition of the present invention.

In a further example, the present invention provides a method for identifying a polymer having suitable bactericidal or antimicrobial activity in which a hydrophilic first comonomer is polymerized to a second comonomer to form a bactericidal or antimicrobial polymeric composition, where the polymeric composition is determined to have suitable bactericidal or antimicrobial activity if the polymeric composition has a higher bactericidal or antimicrobial activity in an aqueous solution than either of the hydrophilic first comonomer or second comonomer alone (or treated similarly as the polymeric composition).

In yet another example, the present invention provides an article comprising a polymeric composition posited on a surface of a medium. The polymeric composition is formed from a hydrophilic first comonomer polymerized to a second comonomer. The hydrophilic first comonomer comprises a methacrylate comonomer. The second comonomer comprises quaternized poly(4-vinylpyridine). The medium is selected from the group consisting of catheters, needles, sutures, stents, implantable medical devices, contact lenses, root canal fillers, wound dressings, burn dressings, tissue culture plates, fibers and paper. Preferably the hydrophilic first comonomer is poly(ethyleneglycol) methacrylate or hydroxyethylmethacrylate and the medium is fibers or paper.

Applications for the inventive compositions include their use in catheters, stents, fibers, paper and other implantable medical devices, contact lenses, root canal fillers, wound dressings, and the like.

DETAILED DESCRIPTION

Figure 1:
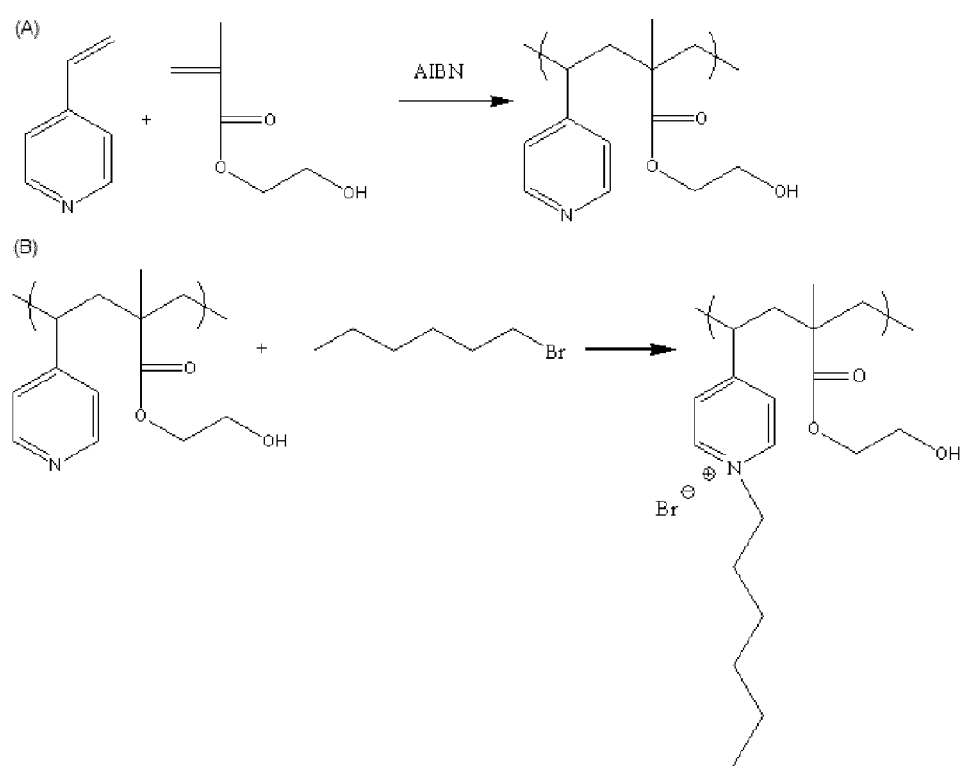
FIG. 1 is a schematic showing (A) the radical polymerization of P(VP-co-HEMA) and (B) quaternization of P(VP-co-HEMA)-HB.

In order to provide a more clear and consistent understanding of the specification and claims, the following definitions are provided. Unless defined otherwise, all technical and scientific terms have the same meaning as is commonly understood by one of skill in the art to which this invention belongs.

The term "monomer" refers to a relatively simple compound, usually containing carbon and of low molecular weight, which can react to form a polymer by combining with itself or with other monomers.

The terms "polymer" and "polymeric composition" are used interchangeably to denote a product of a polymerization reaction, and are inclusive of homopolymers, copolymers, terpolymers, etc.

The terms "polymerization" and "polymerization reaction" are inclusive of homopolymerizations, copolymerizations, terpolymerizations, and the like, and include all types of copolymerizations such as random, graft, block, and the like. In general, the polymers in the bactericidal or antimicrobial composition on may be prepared in accordance with any suitable polymerization process, including slurry polymerization, solution polymerization, emulsion polymerization, gas phase polymerization, and high pressure polymerization processes.

The term "comonomer" refers to a monomer, copolymer, or polymer which can copolymerize with itself or with at least one different monomer, copolymer, or polymer in a copolymerization reaction, the result of which can be a polymer, copolymer or polymeric composition.

The term "copolymer" refers to a polymer which can copolymerize with itself or with at least one different comonomer, polymer, or copolymer in a polymerization reaction or it can refer to a product resulting from a polymerization reaction of two comonomers. The copolymer may be identified or named in terms of the monomer(s) from which the copolymer is produced.

The terms "corresponding comonomer," "corresponding copolymer," and "corresponding polymer" are used to relate comonomers, copolymers, or polymers, respectively, sharing a common set of monomeric units between e.g., distinct polymeric compositions. The common comonomers, copolymers, or polymer need not be identical in terms of the molecular weight(s) or molar ratio(s) of commonly shared monomeric units.

The phrase "corresponding molecular weight" is used to relate molecular weight(s) of corresponding comonomers, copolymers, or polymers, respectively, in distinct polymeric compositions in which the common comonomers, copolymers, or polymers differ from one another by molecular weight(s) or commonly shared monomeric units within the corresponding comonomer, copolymer or polymer.

The phrase "corresponding molar ratio" is used to relate molar ratio(s) of corresponding comonomers, copolymers, or polymers, respectively, in distinct polymeric compositions in which the common comonomers, copolymers, or polymers differ from one another by molar ratio(s) or commonly shared monomeric units within the corresponding comonomer, copolymer or polymer.

The term "bactericidal" is used to interchangeably denote any one of the following: (i) a comonomer, polymer, copolymer, polymeric composition suitably formulated to kill, reduce the growth, number, viability and/or metabolic activity of one or more bacteria; (ii) a material, substance, medium, device, or area treated with a bactericidal comonomer, polymer, copolymer, polymeric composition so as to kill, reduce the growth, number, viability and/or metabolic activity of one or more bacteria.

The term "antimicrobial" is used interchangeably denote any one of the following: (i) a comonomer, polymer, copolymer, polymeric composition suitably formulated to kill, reduce the growth, number, viability and/or metabolic activity of one or more bacteria, fungi, protozoans, or viruses; (ii) a material, substance, medium, device, or area treated with an antimicrobial comonomer, polymer, copolymer, polymeric composition so as to kill, reduce the growth, number, viability and/or metabolic activity of one or more bacteria, fungi, protozoans, or viruses.

The terms "microorganism" and "microbe" are used interchangeably to denote microscopic living organisms including for example, bacteria, fungi, protozoans, and viruses.

The term "aqueous solution" refers to a solution in which water is the solvent.

The term "medium" refers to a treatable material, treatable substance, treatable device, or treatable area in which "treatable" refers to a capacity to be rendered bactericidal or antimicrobial by a bactericidal or antimicrobial comonomer, polymer, or copolymer. A treatable medium may have a defined physical form, but may include liquid (e.g., water, aqueous solution) or gaseous materials (e.g., air) also.

The phrases "significantly reducing the growth of bacteria" and "significantly reducing bacterial growth" are used interchangeably to denote one or more of the following conditions, including (i) a condition in which the metabolic activity of at least 50% of the microorganisms of a particular type exposed to a treated medium is terminated or reduced compared to bacteria of that particular type exposed to an untreated medium over a fixed period of time; (ii) a condition where there is 50% or less of one or more bacterial types present in and/or on a treated medium compared to the number of bacteria exposed to an untreated medium; and/or (iii) a condition resulting when one or more types of bacteria adhere 50% less to a treated medium compared to an untreated medium. The degree of bacterial growth reduction with respect to conditions (i)-(iii) may range from 50% to greater 99.9%.

The phrase "significantly bactericidal" denotes a comonomer, polymer, copolymer, composition, polymeric composition, material, substance or treated area in which the bactericidal comonomer, polymer, copolymer, composition, polymeric composition, material, substance or treated area is suitably formulated to significantly reduce the growth, number, viability and/or metabolic activity of bacteria by at least 50%.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

A bactericidal or antimicrobial polymeric composition of the present invention includes a hydrophilic first comonomer polymerized to a second comonomer, where the polymeric composition is more soluble and/or more bactericidal or antimicrobial in an aqueous solution than either of the first comonomer or the second comonomer alone. The polymeric composition of the present invention were found to have unexpected hydrophilizing and/or wettabiliy properties providing enhanced bactericidal or antimicrobial activity compared to either comonomer alone.

The second comonomer may be inherently bactericidal or antimicrobial or it may be rendered bactericidal or antimicrobial after a subsequent step (e.g., polymerization) and/or chemical modification (e.g., quaternization) of alkyl groups. Where the polymeric composition is further modified by chemical modification, such as quaternization, preferably, the polymeric composition is more hydrophilic and/or bactericidal or antimicrobial than a similarly modified (by e.g., quaternization) second comonomer alone.

Bactericidal or antimicrobial comonomers or those capable of being rendered bactericidal or antimicrobial are copolymerized to a hydrophilizing comonomer. Exemplary second comonomers for polymerization to a hydrophilizing comonomer may include a variety of vinyl monomers capable of free radical polymerization and/or quaternization. Accordingly, these comonomers may include, but are not limited to, vinyl amines, such as N,N-dimethylvinylamine; allyl amines; vinyl esters, such as vinyl acetate; alkyl acrylates; and vinyl chloride. In a preferred embodiment, a pyridinium-type comonomer, such as vinyl pyridine or 4-vinylpyridine, is quaternized after polymerization to a hydrophilizing comonomer.

The second comonomer composition may include or be chemically linked to a suitable bactericidal or antimicrobial moiety, including, but not limited to polycationic species, polycationic derivatives or combinations therefrom. Polycationic species may contain two or more quaternary ammonium groups with a molecular weight ranging from several hundred Daltons to a few hundred thousand Daltons. The quaternary ammonium groups may be part of a ring or they may be acyclic. Examples include but are not limited to: polyionenes, poly(diallyldimethylammonium chloride), dimethylamine-epichlorohydrin copolymers and imidazole-epichlorohydrin copolymers. Suitable bactericidal or antimicrobial comonomers for use in the present invention may include the quaternary ammonium group-containing polymers disclosed in U.S. Pat. No. 4,482,680, which are incorporated by reference herein.

Polycationic species may contain two or more amine groups. The amine groups can be primary, secondary, tertiary, or mixtures thereof. The amine groups may be part of a ring or they may be acyclic. Examples include but are not limited to: polyethyleneimines, polypropyleneimines, polyvinylamines, polyallylamines, polydiallylamines, polyamidoamines, polyaminoalkylmethacrylates, polylysines, and mixtures thereof.

The polycationic species may also be a modified polyamine with at least one amine group substituted with at least one other functional group. Examples include ethoxylated and alkoxylated polyamines and alkylated polyamines. Other suitable bactericidal or antimicrobial comonomers or those that may be rendered bactericidal or antimicrobial may be identified and/or used in accordance with the applications and objectives set forth in the specification and claims.

Quaternization may be carried out using alkylating agents, including but not limited to alkyl halides (such as hexyl bromide), alkyl sulfonates, alkyl mesylates, alkyl tosylates, or other alkylating agents possessing a suitable leaving group. Quaternization reduces self-polymerization of the bactericidal or antimicrobial comonomer upon polymerization with the hydrophilizing comonomer. Quaternization may confer increased bactericidal or antimicrobial activity and is typically carried out after polymerization, since quaternized polymers are unpolymerizable.

Quaternized alkyl groups and/or other cationic chains may be attracted to and/or promote interaction and penetration negatively charged bacterial cell walls on account of their lipophilic nature. Alkyl chain lengths of quaternizing agents and overall hydrophilic/lipophilic balance may affect bactericidal or antimicrobial activity of the polymeric compositions of the present invention. Accordingly, these variables may be modified to optimize or improve bactericidal or antimicrobial activity of the polymeric compositions.

Hydrophilizing comonomers of the present invention confer increased wettability or hydrophilicity to one or more surfaces of the polymeric composition in aqueous solutions, including water. Preferably, the polymeric composition is more wettable than a bactericidal or antimicrobial comonomer or a comonomer rendered bactericidal or antimicrobial by quaternization, such as poly(4-vinylpyridine). Suitable hydrophilizing monomers or copolymers, may include, but are not limited to, ethylene glycol (ethylyene oxide); polyethylene glycol derivatives, including poly(ethyleneglycol) methacrylate (PEGMA), poly(ethyleneglycol) acrylate, and vinyl polyethylene glycol; vinyl acetate; poly(vinyl alcohol); vinyl pyrrolidone and poly(vinyl pyrrolidone); vinyl pyrrolidinone and poly(vinyl pyrrolininone); vinyl oxazoline and poly(vinyl oxazoline); vinyl foramide and poly(vinyl foramide); hydroxyalkyl acrylates and hydroxyalkyl methacrylates, such as hydroxyethyl methacrylate (HEMA) and hydroxyethyl acrylate; methacrylamide; acrylamide and methacrylamide based monomers, such as acrylamide, N,N-dimethyl acrylamide, N-ethyl acrylamide, N-isopropyl acrylamide, and hydroxymethyl acrylamide; monomers containing one or more of the following functional groups: hydroxy, amino, ammonium, ether, carboxylate, amide, and sulfoamide groups; and combinations or copolymers thereof. polyvinyloxazolines Hydrophilic polymeric compositions and methods for hydrophilizing polymeric materials, including the use of high energy treatments, are disclosed in U.S. Pat. Appl. No. 20050008839, the contents of which are expressly incorporated by reference in their entirety, also may be used.

Preferably, the hydrophilizing comonomer is biocompatible. Standard assays may be utilized to evaluate biocompatibility, including but not limited to viability/cytotoxicity mammalian cell assays and the like. Representative hydrophilizing comonomers or copolymers include hydroxyethylmethacrylate (HEMA) and poly(ethyleneglycol) methacrylate (PEGMA).

HEMA is widely used in biomedical applications and devices, most prominently soft contact lenses. HEMA, with 37.8% water per weight, is typical of hydrogels. Preferably, the molar ratio of HEMA comonomer in the polymeric composition is equal to or greater than about 90 to 1.

PEGMA is a biocompatible polymer which possesses several important properties, such as good solubility in both organic and aqueous media, low toxicity, immunogenicity and nonbiodegradability.

Preferably, the molar molecular weight of PEGMA comonomer in the bactericidal or antimicrobial composition is equal to or greater than 300, more preferably between about 300 and about 2000, including but not limited to 1100. Preferably, the molar ratio of PEGMA comonomer in the polymeric composition is equal to or less than about 10 to 1; equal to or less than about 25 to 1; equal to or greater than about 75 to 1; equal to or greater than about 95 to 1; equal to or greater than about 99 to 1.

Hydrophilicity or wettability can be evaluated by any suitable methodology known in the art, including contact angle testing and tensionometry testing. Contact angle testing of polymeric compositions may be carried out by dip coating microscope slides in solutions with copolymer dissolved in chloroform and methanol and obtaining contact angle measurements using e.g., a Ramé-Hart Advanced Goniometer. Contact angles may be characterized as advancing or receding, the difference being whether or not the angle is taken when moving onto a dry surface or moving off a wet surface. Advancing angles may be used for surface energy determinations, receding angles for characterizing other surface characteristics.

Polymeric bactericidal or antimicrobial compositions may be rendered hydrophilic by engineering them to have advancing contact angles with water of less than or equal to about 90 degrees, preferably less than or equal to about 45 degrees, more preferably less than or equal to about 30 degrees, less than or equal to 15 degrees after 30 seconds of spreading.

The disclosed bactericidal or antimicrobial compositions are suitably formulated to significantly reduce the growth, number, viability and/or metabolic activity of bacteria or microorganisms. A bactericidal or antimicrobial composition may be formulated to significantly reduce bacterial or antimicrobial growth from a treated medium by a factor of at least 50%. Further, a bactericidal or antimicrobial composition may be formulated to significantly reduce bacterial or microbial growth from a treated medium by at least 60%, by at least 70%, by at least 80%, by at least 90%, by at least 95%, by at least 99%, or by at least 99.9%.

The bactericidal or antimicrobial composition may be applied as a coating to at least one portion or surface of a medium or medical device, such as a catheter, or an implantable medical device, such as a stent. Various methods may be used to apply the comonomers or bactericidal or antimicrobial polymers as a coating to the surface of the medical device. Suitable methods for applying coatings may include, but are not limited to the methods disclosed in U.S. Pat. No. 5,509,899 and U.S. Pat. No. 6,221,425, the contents of which are expressly incorporated by reference in their entirety.

Comonomers may be applied to a surface and subsequently polymerized. Alternatively, the bactericidal or antimicrobial polymer composition may be applied directly to the surface of the medical device. In particular, one or more comonomers or bactericidal polymers may be combined with water and sprayed onto the medical device. Alternatively, the medical device may be dipped into a solution containing the bactericidal or antimicrobial polymer. The comonomer or bactericidal or antimicrobial polymer may be present in the solution in an amount from about 50% to about 98% by weight, particularly from about 70% to about 90% by weight, and applied to the surface of the medical device.

The viscosity of the monomeric or polymeric solution can be adjusted depending upon the particular application and circumstances. In general, when dipping the medical device into the solution, higher viscosities will cause more of the bactericidal or antimicrobial polymer to remain on the surface of the device. Thus, if thicker coatings are desired, the viscosity can be increased. The viscosity of the solution can be increased by minimizing the amount of water in the solution. Additionally, thickeners, such as a polyacrylamide, can be added to the solution. The viscosity of the solution may also be increased by partially polymerizing the monomer.

In another example, the present invention provides an antimicrobial or antibacterial composition comprising an antibacterial polymeric composition and water. Other solvents may be added to the composition including alcohols such as ethanol, for example, if desired, but the addition of an alcohol is not necessary for the antimicrobial or antibacterial properties of the composition. The antimicrobial or antibacterial composition is preferably in liquid form and may be applied to the skin of a human or mammal. Because the copolymer of the present invention will not evaporate and remains present for some time after application, the antimicrobial or antibacterial composition provides long-lasting antimicrobial effects. Compositions which make which make use of quickly evaporating ethanol for the antimicrobial properties do not provide long-lasting antimicrobial effects and can also dry out the skin.

To ease application and improve aesthetics, a thickener or gelling agent may be added to the composition. Any thickener or gelling agent which is compatible with the antibacterial or antimicrobial polymeric composition may be used. Preferably the thickener is suitable for human or mammal use, more preferably the thickener is approved by the Food and Drug Administration (FDA). Without wishing to be bound by theory, the formation of an electrolyte between the antibacterial or antimicrobial polymeric composition and the thickener diminishes efficacy. Because the antibacterial or antimicrobial polymeric composition comprises a polycation chain, it is desirable to use a neutral or cationic thickener.

Examples of cationic thickeners include for example, aminoalkyl methacrylates, alkylaminoalkyl methacrylates, dialkylaminoalkyl methacrylates, aminoalkyl acrylates, alkylaminoalkyl acrylates, dialkylaminoalkyl acrylates. Preferably the cationic thickener is an aminoalkyl methacrylate, more preferably aminoethyl methacrylate.

Examples of neutral thickeners include natural gums, including for example carrageenans, acacia, guar, guargum, hydroxypropyl guar, karaya gum, kelp, locust beangum, tragacanth gum, xanthan gum, alginates and the like; pectins; gelatins; flours and starches including for example, oat flour, potato starch, wheat flour, wheat starch, and the like; agars; dextrins; and casein; cellulose derivatives, including for example, carboxymethyl hydroxyethyl cellulose, cellulose, hydroxybutyl methylcellulose, hydroxyethyl cellulose, hydroxypropyl cellulose, hydroxypropyl methyl cellulose, methyl cellulose, microcrystalline cellulose, and the like; and poly(vinyl pyrrolidone). Preferably, the thickener is a cellulose derivative, more preferably hydroxyethyl cellulose.

The amount of thickener present in the composition depends upon the desired viscosity of the composition. To achieve the desired viscosity, the thickener may be present in the composition in an amount from about 1.3% wt. % to about 25 wt. % of the total composition, dependent on the viscosifying agent or agents chosen.

The antimicrobial or antibacterial composition may be used by itself or as an additive to another product. When used by itself, the composition is applied to the skin, preferably the hands, in an amount from about 1 to about 10 mL, preferably about 2 to about 5 mL. The composition is rubbed over the skin to distribute the composition for absorption onto the skin.

In another example, the present invention provides articles comprising an antibacterial or antimicrobial polymeric composition of the present invention posited on a surface of a medium. The medium may be any article in which it is desirable to render a surface or part of a surface antibacterial or antimicrobial, including for example, catheters, needles, sutures, stents, implantable medical devices, contact lenses, root canal fillers, wound dressings, burn dressings, tissue culture plates, fibers and paper. The antibacterial or antimicrobial polymeric composition may be posited on a surface by applying the polymeric composition which comprises water and optionally another solvent and allowing the water or other solvent to evaporate. For example, a sheet of paper may be coated by forming a polymeric composition in water and optionally another solvent which does not dissolve paper, applying the polymeric composition to the entire surface of the paper and allowing the water or other solvent to dry, thereby forming a polymer coating over the entire surface of the paper.

Alternatively, the hydrophilic first comonomer and second comonomer may be grafted to the surface of a medium by plasma grafting and then quaternized with an alkyl bromide to form the antimicrobial surface. For example, 4-vinyl pyridine and poly(ethylene glycol) methyl ether methacrylate may be grafted to the surface of paper via plasma grafting and then quarternized with bromohexane to form the antimicrobial surface. In another example, the surface or more specifically paper surface may be acylated by reacting it with 4-bromobutyrylchloride while immersed in an appropriate solvent. The polymeric composition, formed for example, from 4-vinyl-pyridine and poly(ethylene glycol) methyl ether methacrylate may then be quaternized by the surface alkyl bromide groups.

The antibacterial or antimicrobial polymeric composition may be incorporated into a natural or synthetic fiber. For example, the polymeric composition may be incorporated on or into fibers used for clothing or paper. Paper made from such fiber may be suitable as a food wrapping, part of a temporary wound dressing, as a disinfectant wipe, or for paper used in medical settings such as doctors' offices and hospitals including magazines.

The polymeric composition may be soluble or insoluble, depending on whether the desired product should be able to release the antibacterial or antimicrobial polymeric composition or retain the antibacterial or antimicrobial polymeric composition. In some aspects, the polymeric composition may be temporarily posited on the fibers for release onto a desired surface or into a desired environment at a later time. For example, a soluble polymeric composition may be used in a disinfectant wipe. The disinfectant wipe, which may be an alcohol based disinfectant wipe, releases the antibacterial or antimicrobial polymeric composition to another surface, imparting long-lasting antimicrobial properties to the applied surface.

In another example, the present invention provides methods for rendering a material or area bactericidal or antimicrobial. In a further example, the present invention provides a method for killing or significantly reducing the number of bacteria or microorganisms on a material or area treated with a bactericidal or antimicrobial composition of the present invention.

Accordingly, in one example, a bactericidal or antimicrobial composition of the present invention is applied to a medium or medical device in an amount sufficient to kill or significantly reducing the number of bacteria or microbes in or on the treated medium compared to an untreated medium. In a further example, a bactericidal or antimicrobial composition according to the present invention is applied to a medium or medical device in an amount sufficient to kill at least one bacterium or microbe or significantly reduce bacterial or microbial growth compared to an untreated medium.

The bacteria may be Gram-positive or Gram-negative. The bactericidal or antimicrobial composition may be included in or coated onto a catheter, stent, implantable medical device, contact lens, root canal filler, or wound dressing. The treated medium may include natural or synthetic materials, implantable devices, or bodily surfaces. The treated medium may be contact with an aqueous environment, such as water or the inside of a patient or other vertebrate organism. Alternatively, the treated medium may be contact with air or air and/or air borne bacteria in an external environment or an enclosed bodily organ, such as lung.

Biocompatibility may be evaluated by any suitable methodology known in the art, including one or more viability/cytotoxicity assays known to those of ordinary skill in the art.

In a further example, the present invention provides a method for identifying a polymer having suitable bactericidal or antimicrobial activity. In this method, a hydrophilizing first comonomer may be polymerized to a second comonomer and a bactericidal or antimicrobial polymeric composition is formed. The bactericidal or antimicrobial polymeric composition may be applied to a medium to form a first treated medium and the medium may be separately treated with the second comonomer used in the first treated medium. The first treated medium and the second treated medium may be separately contacted with a plurality of bacteria or microbes. Whether the first treated medium is more bactericidal or antimicrobial than the second treated medium may be determined.

In a further example, a first polymeric composition and a second polymeric composition differing by molecular weight with regard to one or more corresponding comonomers may be separately applied to a medium and tested to identify a polymeric composition having improved bactericidal or antimicrobial activity.

Alternatively, a first polymeric composition and a second polymeric composition differing by molar ratio of their corresponding comonomers may be varied and may be separately applied to a medium and tested to identify a polymeric composition having improved bactericidal or antimicrobial activity.

In the above disclosed methods, a given polymeric composition may be rendered bactericidal or antimicrobial by quaternization after polymerizing the hydrophilizing first comonomer to the second comonomer. Accordingly, the quaternized polymeric composition would be deemed suitable for use in a bactericidal or antimicrobial composition if a medium containing or treated with the quaternized polymeric composition is more hydrophilic and/or bactericidal or antimicrobial than the same medium containing or treated with the quaternized second comonomer alone.

Bactericidal or antimicrobial activity may be evaluated using any suitable testing methodology used in the art, including, but not limited to, luminescence, optical density, or microscopic evaluation of bacterial or microbial growth or viability of coated and/or stained microscopic slides, plates or cultures.

The following examples illustrate features in accordance with the present invention, and are provided solely by way of illustration. They are not intended to limit the scope of the appended claims or their equivalents.

EXAMPLES

1. Radical Polymerization and Quaternization. Copolymers possessing suitable bactericidal properties and a suitable hydrophilicity/biocompatibility profile were obtained using a quaternized polymeric composition synthesized from 4-vinylpyridine and a biocompatible, hydrophilic comonomer, such as hydroxyethylmethacrylate (HEMA) or poly(ethyleneglycol) methacrylate.

Copolymers were synthesized by radical copolymerization with AIBN as initiator. The reactants were stirred at 70° C. for 48 hours under flowing $N_2$ to prevent oxidation. As the monomer contents were varied, the AIBN proportion was held constant to a massic ratio VP+PEGMA:AIBN equal to 22:1. To investigate the effects of hydrophilization, seven different compositions of VP with PEGMA300, PEGMA1100 and HEMA were synthesized, containing a molar percentage of VP of 10, 25, 50, 75, 90, 95 and 99.

Copolymers were quaternized with a 3-fold excess of hexyl bromide (HB) in a mixture of chloroform and methanol by reflux for 48 hr. They were precipitated in hexane, recovered and dried under vacuum. A schematic of the radical polymerization and quaternization process can be seen in FIG. 1.

Synthesis of P(VP-co-HEMA), P(VP-co-PEGMA300) and P(VP-co-PEGMA1100) was followed with FTIR and NMR. Spectroscopy showed that the synthesis was successful and that the quaternization went to near completion and that the resultant products were relatively pure after work-up.

VP, HEMA and PEGMA were purchased from Sigma Aldrich Co. (Milwaukee, USA). To avoid polymerization through heat or light, these monomers were inhibited with hydroquinone (HQ), 4-Methoxyphenol (MEHQ), and 2,6-di-tert-butyl-4-methylphenol (BHT) respectively. The HQ and MEHQ inhibitors were removed by means of trap to trap while BHT was purified from PEGMA by column chromatography on silica gel (70-270 mesh) stationary phase.

2. Antimicrobial Hand Gel

An antimicrobial polymeric composition is prepared by dissolving the polymeric composition in water or a mixture of ethanol and water, such as 70% ethanol/30% water. The thickener is then added, and the resulting mixture is heated with stirring and kept below 70° C. until dissolution.

A P(VP-co-PEGMA300) hand gel was prepared by mixing 0.01 g of P(VP-co-HEMA) with 10 mL of water. Hydroxyethyl cellulose (0.013 g) was added, and the resulting mixture heated to 70° C., then cooled to room temperature.

3. Contact Angle and Bactericidal Testing. To evaluate wettability or hydrophilicity, contact angle tests were conducted by dip coating microscope slides in solutions with copolymer dissolved in chloroform and methanol. Contact angle measurements were obtained on a Ramé-Hart Advanced Goniometer.

Bactericidal tests were performed with a small quantity of the bacteria *Escherichia coli* O157:H7 in which the lux gene was added for luminescence, which provides a measure of metabolic growth or activity. A sample was taken from a culture and placed in contact with the coated slides, by means of a pipette. The intensity of the bioluminescence was recorded as a function of time for two hours with a photomultiplier tube. Reduced bioluminescence correlates with enhanced bactericidal activity.

Figure 2:
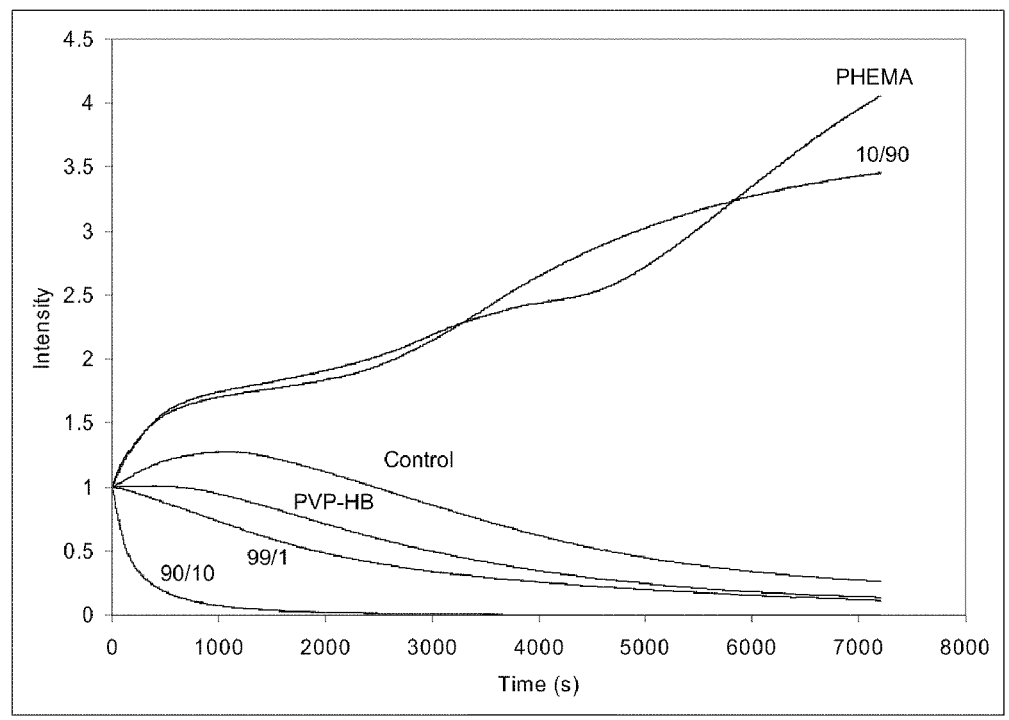
FIG. 2 is graph of bactericidal results for surface testing of P(VP-co-HEMA)-HB.

4. Bactericidal activity of P(VP-co-HEMA). The results of the bactericidal tests on quaternized copolymers of VP and HEMA are shown in FIG. 2. An initial increase of intensity is observed in the control, due to the fast growth of the bacteria, called blooming. After approximately 19 minutes, the intensity starts decreasing as the bacteria start to die. PVP-HB, known to kill bacteria, prevents blooming, as reflected by the fact that the intensity never increases by more than 1 percent. The intensity starts decreasing after only 7 minutes. Since this is much earlier than the control, the death of the bacteria can be attributed to the properties of the polymer. An uninterrupted blooming is observed for a slide coated with PHEMA, and the number of bacteria has quadrupled after two hours, following a lag-log behavior. This indicates that PHEMA by itself is not bactericidal.

P(VP-co-HEMA)-H B 95/5 and P(VP-co-HEMA)-H B 90/10 exhibited enhanced bactericidal activity compared to PVP-HB alone. The luminescence recorded for P(VP-co-HEMA)-HB 99/1, is similar to, but slightly less than that observed for PVP-HB alone. Accordingly, this copolymer, having one molar percent HEMA, displays properties similar to PVP-HB alone. However, a slide coated with P(VP-co-HEMA)-HB 99/1 kills bacteria faster than one coated with PVP-HB.

Figure 3:
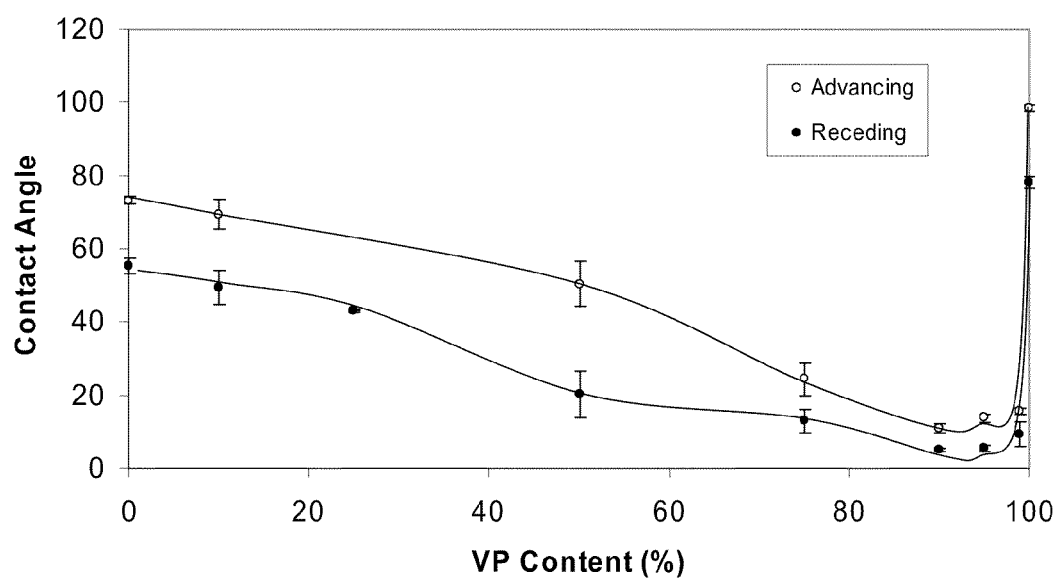
FIG. 3 is a graph of advancing and receding contact angles for P(VP-co-HEMA).

The wettability of dry, vitreous HEMA-based materials was studied by contact angle measurements. The results for both advancing and receding angles are given in FIG. 3. Contact angle measurements showed an increase in hydrophilicity provoked by the copolymerization. The surface energy was found to be minimal for P(VP-co-HEMA) at 90/10 and slightly higher for P(VP-co-HEMA)-HB 99/1. This corresponds to the bactericidal behavior of the polymers and suggests that the wettability plays a significant role in the polymer's effectiveness. Being a hydrogel monomer, HEMA hydrophilizes the copolymer.

Although not wishing to be bound by theory, it is believed that coupling hydrophilization to bactericidal activity in the polymer facilitates enhances bacterial killing, in part because of the water-loving nature of bacteria: a hydrophilic growth medium is better able to support uptake and killing by a hydrophilized bactericidal polymer compared to an unhydrophilized bactericidal polymer. It is further believed that the hydrophilized bactericidal polymers of the present invention to unexpectedly possess enhanced biocompatility characteristics, enhanced stabilization of blood cells compared to saline and decreased absorption to proteins and lipids.

In P(VP-co-HEMA)-HB 90/10, the wettability effect is particularly evident. This polymer exhibits a more optimal bactericidal activity, reflected in the fact that all bacteria were killed in 30 minutes. This further illustrates that that a slide coated with P(VP-co-HEMA)-HB 90/10 copolymer is significantly more bactericidal than pure PVP-HB.

Figure 4:
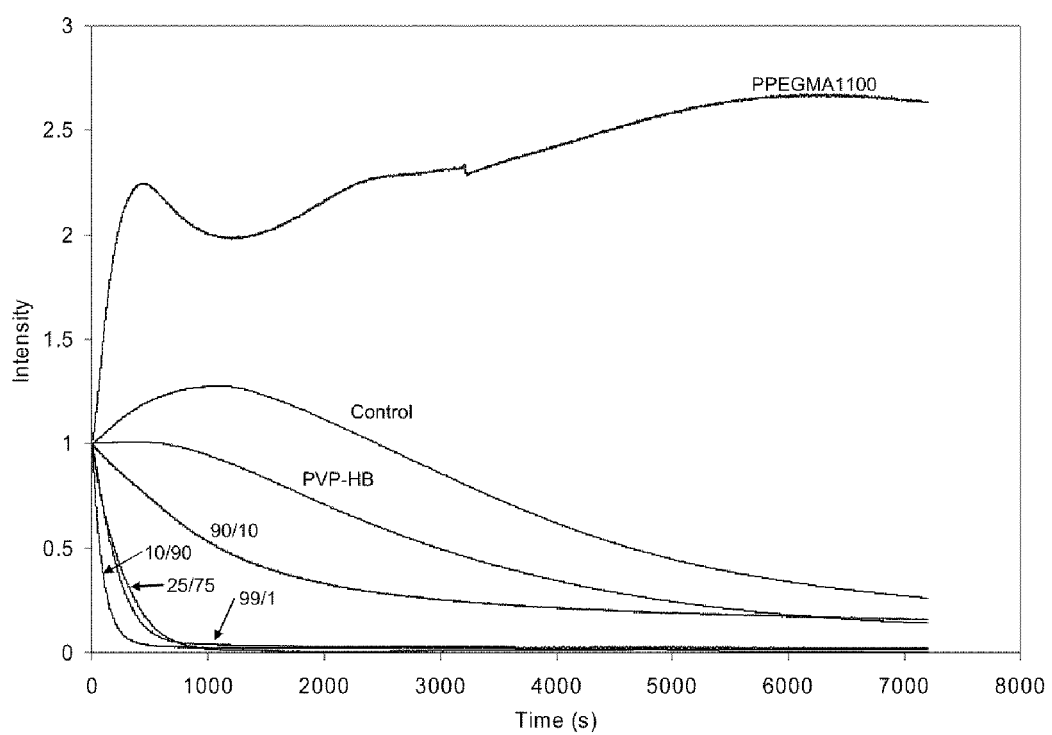
FIG. 4 is a graph of bactericidal results for testing of P(VP-co-PEGMA1100).

5. Bactericidal activity of P(VP-co-PEGMA). The bacterial growth behavior for copolymers with PEGMA1100 can be seen in FIG. 4. Comonomer ratios of 90/10, 25/75, and 10/90 exhibited enhanced bactericidal activity compared to PVP-HB alone. Extremely high bactericidal activity was seen with ratios of 99/1, presumably due to the large fraction of VP and improved wettability from PEGMA1100. Copolymers with ratios ranging from 95/5 to 50/50 displayed bacterial results similar to PVP-HB.

P(VP-co-PEGMA1100)-HB 25/75 and 10/90 displayed a surprisingly high antibacterial activity. Although counterintuitive, this fact can have several explanations. The molecular weight of P(VP-co-PEGMA1100)-HB 10/90 is much higher than other copolymer formulations of this system. This could increase bactericidal activity, because the copolymer possesses more alkyl tails to traverse the bacterial membranes. The enhanced water wettability of the polymer may enable the polymer to better dissolve in and/or surround the bacteria in an aqueous medium, so as to facilitate more efficient bacterial killing.

PPEGMA300 (graph not shown) alone does not kill bacteria and actually improves growth due to its biocompatibility and hydrophilicity. The improved biocompatibility and hydrophilicity is carried over into the P(VP-co-PEGMA300) copolymers with ratios from 0/100 to 50/50 thereby improving bacterial growth. However, for ratios greater 50/50, bactericidal activity was observed. The optimum balance between spreading and VP content was found to be 75/25, in which half the bacteria were killed in the first 15 minutes.

Overall, the bactericidal behavior of the PEGMA300 based polymers were reduced compared to PEGMA1100 based polymers.

PEGMA1100 has a significantly larger PEG size than PEGMA300. A smaller fraction of PEGMA1100 is thus necessary to hydrophilize P(VP-co-PEGMA1100). However, even for some similarly hydrophilized polymers, the PEGMA1100 materials exhibit superior bactericidal activity, possibly due to the enhanced protein resistance imparted by longer PEG chains in the polymers.

The enhanced bactericidal activity exhibited by the HEMA and PEGMA copolymers appears to result from enhanced wettability in aqueous solutions, allowing the polymer to better surround and/or gain access to the bacteria, so as to enhance bacterial killing.

Figure 5:
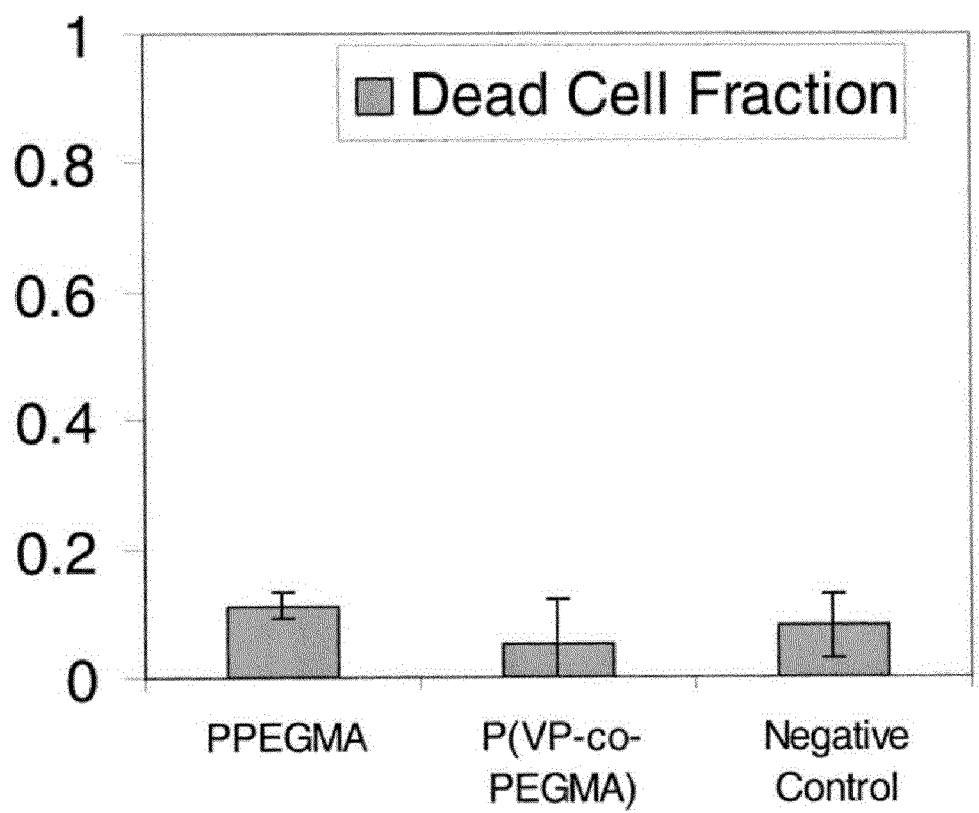
FIG. 5 is a graph of dead epithelial cells as a function of PPEGMA, P(VP-co-PEG MA) or control polymer.

6. Cytotoxity of P(VP-co-PEGMA). A viability/cytotoxicity assay may be used to evaluate biocompatibility of the bactericidal polymers for mammalian cells. In particular, FIG. 5 shows that an exemplary bactericidal PEGMA 1100 copolymer is non-toxic to mammalian cells. Corneal epithelial cells were seeded onto polystyrene culture plates in phosphobuffered saline solution (PBS; pH 7.2) at a density of 3,500 cells/cm$^2$ for 24 hrs at 37° C. The cells were co-incubated for 4 hrs. with quaternized P(VP-co-PEGMA 1100) copolymer or PPEGMA control polymer in PBS at a concentration of 2.5 mg/ml, along with a PBS negative control media.

Live cells were distinguished from dead cells using a fluorescence-based LIVE/DEAD viability/cytotoxicity assay system (Molecular Probes, Invitrogen Detection Technologies). The assay system includes two probes, calcein AM, a fluorogenic esterase substrate producing a green fluorescent product in live cells having intracellular esterase activity, and ethidium homodimer-1, a high-affinity, red fluorescent dye only able to pass through and stain the compromised membranes of dead cells. FIG. 5 plots the fraction of dead epithelial cells as a function of added bactericidal polymer or polymer control. As shown in FIG. 5, treatment of epithelial cells with the bactericidal P(VP-co-PEGMA) polymer did not exhibit a statistically significant level of epithelial cell killing over that of the PEGMA polymer or PBS negative controls.

It is to be understood that the above-described polymers and methods for their use are merely representative embodiments illustrating the principles of this invention and that other variations in the polymers or methods, may be devised by those skilled in the art without departing from the spirit and scope of this invention. The foregoing detailed description and accompanying drawings have been provided solely by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A composition comprising a water-soluble random copolymer formed from a hydrophilic first comonomer having an acrylate moiety comprising at least one of hydroxyethylmethacrylate, poly(ethylene glycol) methacrylate and poly(ethylene glycol) methyl ether methacrylate, and a second pyridinium-type comonomer containing a nitrogen atom and a vinyl moiety, wherein the first comonomer and the second comonomer are chemically bonded through the acrylate moiety of the first comonomer and the vinyl moiety of the second comonomer, wherein said nitrogen atom is quaternized with an alkyl moiety such that said polymer is polycationic, and wherein the amounts of the first comonomer and the second comonomer provide said water-soluble random copolymer with
  i. improved bactericidal activity as compared to the first comonomer or a homopolymer formed from the first comonomer; and
  ii. improved bactericidal activity as compared to the second comonomer or a homopolymer formed from the second comonomer.

2. The composition of claim 1 further comprising a halide anion.

3. The composition of claim 2 wherein the anion comprises a bromide anion.

4. The composition of claim 1 wherein the alkyl moiety comprises a hexyl moiety.

5. The composition of claim 4 further comprising a halide anion.

6. The composition of claim 5 wherein the halide anion comprises a bromide anion.

7. The composition of claim 1, wherein the second comonomer comprises 4-vinylpyridine.

8. The composition of claim 7 wherein the first comonomer comprises poly(ethylene glycol) methacrylate having a molecular weight of at least about 300 Daltons.

9. The composition of claim 8 wherein the molecular weight of poly(ethylene glycol) methacrylate is less than about 2000 Daltons.

10. The composition of claim 7 wherein the first comonomer comprises hydroxyethylmethacrylate.

11. The composition of claim 7 further comprising a halide anion.

12. The composition of claim 11 wherein the anion comprises a bromide anion.

13. The composition of claim 7 wherein the alkyl moiety comprises a hexyl moiety.

14. The composition of claim 13 further comprising a halide anion.

15. The composition of claim 14 wherein the halide anion comprises a bromide anion.

* * * * *